United States Patent
Argyle et al.

[11] Patent Number: 6,141,093
[45] Date of Patent: Oct. 31, 2000

[54] METHOD AND APPARATUS FOR LOCATING POWER PLANE SHORTS USING POLARIZED LIGHT MICROSCOPY

[75] Inventors: Bernell E. Argyle, Hopewell Junction; Arnold Halperin, Cortlandt Manor; Michael E. Scaman, Goshen; Edward J. Yarmchuk, Mahopac, all of N.Y.

[73] Assignee: International Business Machines Corporation, Armonk, N.Y.

[21] Appl. No.: 09/139,515

[22] Filed: Aug. 25, 1998

[51] Int. Cl.[7] .............................. G01N 21/00; G01R 27/14
[52] U.S. Cl. ...................... 356/237.1; 324/73.1; 324/523; 324/524; 324/752; 324/537; 324/765
[58] Field of Search ..................... 356/375, 394, 356/237.1, 364, 369, 365; 324/73.1, 523, 524, 537, 158.1, 763, 96, 765, 501, 750, 752, 754; 250/225, 559.45, 559.46

[56] References Cited

U.S. PATENT DOCUMENTS

| | | | |
|---|---|---|---|
| 5,087,874 | 2/1992 | Robinson | 324/73.1 |
| 5,640,099 | 6/1997 | Sanada | 324/752 |
| 5,844,249 | 12/1998 | Takano et al. | 250/225 |
| 5,936,408 | 8/1999 | Scaman | 324/537 |

*Primary Examiner*—Hoa Q. Pham
*Attorney, Agent, or Firm*—Ratner & Prestia; Tiffany L. Townsend

[57] ABSTRACT

An apparatus and corresponding method for detecting, locating, or defining a short in a thin-film module. The apparatus includes a mechanical fixture supporting the module. A current source provides a current pulse to the module which produces a magnetic field and heating nearby the short which turns on and off as the pulsed current in the short turns on and off. Polarized light is directed onto the module, with an intermediate element disposed between the module and the source of the polarized light. The intermediate element may be a stress birefringent coating (e.g., a polyimide insulating layer) disposed on the module and onto which the polarized light is directed. The sample is rotated 0 to 45 degrees to maximize the birefringent effect. Alternatively, the intermediate element may be a magneto-optical Faraday rotator. A microscope is used to observe the module, facilitating identification of a short by the twisting of the polarization of the light as the short expands and shrinks in response to the heating or in response to the localized magnetic field. The preferred rotator is a composite having a garnet substrate, an iron garnet film disposed on the substrate, and a thin aluminum mirror layer disposed on the iron garnet film. The apparatus and method of the present invention have several applications.

20 Claims, 11 Drawing Sheets

METHOD AND APPARATUS FOR LOCATING POWER PLANE SHORTS USING POLARIZED LIGHT MICROSCOPY

TECHNICAL FIELD

The present invention relates generally to thin film inspection, test, and repair and, more particularly, to finding the location of power plane shorts on MCM-D modules (multi-chip modules with thin films) or power plane shorts on PCBs (printed circuit boards) to avoid yield loss and to increase diagnostic ability for process learning purposes using optical microscopy with nearly crossed polarizers.

BACKGROUND OF THE INVENTION

Conventionally, after all thin film layers on a multichip module (MCM) have been fabricated, a full electrical test is performed to confirm the integrity of the completed wiring. If any defect is detected at this stage, an after-thin-film (ATF) repair is performed to correct the defective nets.

FIG. 1 shows a plan view of a typical MCM 100. In FIG. 1, chips 102, 104, 106, 108, 110, 112, and 114 are mounted to the top surface metallurgy (TSM) of MCM 100 using a Controlled-Collapsed-Chip-Connection (C4) configuration (not shown in this Figure). Seven chip locations are shown in FIG. 1. MCMs are not limited to this configuration, however, and may be any number of chips depending on the requirements of the application. Before mounting the chips 102 through 114, MCM 100 is tested to ensure that no wiring defect such as an open or a short exists in MCM 100. If a wiring defect is found, the MCM must be repaired. Shorts between power planes are a particularly difficult problem in packaging both from a yield perspective and from a diagnostic perspective. Tests for power plane shorts are relatively simple, yet such shorts are difficult to locate and are an important class of critical defects.

The conventional ATF repair strategy discards the entire original net wiring and reconstructs new net wiring using the top surface repair lines, modifying their lengths to match the required electrical properties of the deleted wiring net. This conventional ATF repair method had worked well for traditional thin-film MCM manufacturing. For close tolerance thin-film MCM products, however, a drawback of this conventional repair process is that product yield is adversely affected if the number of nets requiring repair exceeds the number of available repair nets on the TSM.

Referring again to FIG. 1, a typical pair of wiring nets 116, 118 is shown. For illustrative purposes, it is assumed that a short circuit exists between wiring nets 116, 118. The conventional repair process deletes all of wiring nets 116, 118 by cutting wiring nets 116, 118 at C4 location 120. In this example, wiring nets 116, 118 are cut (also called deletes) at sites 122, 124, 126, 128, 130, 132, 134, 136, 138, 140, 142, 144, 146, and 148. The deleted wiring nets 116, 118 must be replaced using the TSM repair net (shown in FIG. 2A).

FIGS. 2A and 2B show a typical TSM repair net 200 for the MCM of FIG. 1. In FIG. 2A, repair net 200 has x-lines 202 and y-lines 204. As shown in FIG. 2B, within the gridwork of repair net 200 are C4 connections 206 for each chip 102, 104, 106, 108, 110, 112, and 114 mounted on MCM 100.

FIG. 2C shows an x-ray view of a five-layer MCM and FIG. 2D is a partial side view of MCM 100 illustrating the layered structure of MCM 100. In FIG. 2C, successive layers form MCM 100. Typical layers include ground layer 208, power layer 210, x-layer 212, and y-layer 214. An additional layer, top layer 216 (shown in FIG. 2D), contains repair net 200 and C4 connections 206. It is apparent from FIG. 2C that repair of an internal short circuit between any two x-layer lines or y-layer lines is a formidable task. For this reason, conventional repair processes deleted defective nets at the top layer 216.

As mentioned above, conventional ATF repair is based on full repair. That is, the entire internal structure of a defective net is removed at its C4 connections 206. An entirely new set of wiring is reconstructed using repair net 200 and connected to the C4 connections 206 on the TSM. These full repairs are expensive and time consuming. Full repairs are often necessary, however, because frequently the location of the defect in the defective net is unclear and the construction of a new net is the only practical way to repair the defective net.

Generally, power-to-power shorts or defects such as opens or shorts on critical input-output (IO) nets, such as IO nets connected to a BSM (bottom side metallurgy) IO pad which will be connected to a BSM pin, must be repaired at or near the wiring level manufactured. Otherwise, the part will be scrapped when the defect is discovered later at a more costly level of build when repair may no longer be possible or where the defect may no longer be visible due to layers of metal and insulator above it.

In the case of multilayer thin-film MCMS, the best opportunity to diagnose, locate, and repair defects in the thin-film structures occurs after each metal layer is added. The extraordinarily complex configuration of the thin film structures and the high topology render it difficult, however, to pinpoint defects such as shorts even when the approximate location of the short is known.

Historically, infrared (IR) techniques have been used to locate power plane shorts on electronic packaging devices such as printed circuit boards. A current is directed through the short, heating the area around it, and an IR camera is used to approximate the location. These techniques may be destructive and often require special optics not readily available or accessible on the manufacturing floor. In addition, the device may provide a heat sink making it difficult to obtain a significant difference in temperature between the short and the background.

Automated optical inspection (AOI) techniques provide another approach used to locate power plane shorts. AOI techniques require large, relatively expensive inspection devices. In addition, although such techniques work well for many classes of defects, there are always some classes of defects which escape optical detection. Optical techniques will tend to be particularly poor for unusual defects such as inter-level shorts (ILS) not clearly visible from the top of the device. Manual inspection on extremely complex products may likewise be ineffective.

A more recent alternative is to pass a high-frequency current through the defect and approximate the location of the short using a magnetic pickup coil apparatus. Such magnetic induction methods are generally limited in spatial resolution and only approximate the general location of the defect. Further apparatus may be necessary to precisely pinpoint the location of the defect. In addition, magnetic induction techniques assume that an operator can recognize a short once its location is observed under a microscope. There remains a need, therefore, for a technique which can pinpoint the location of a defect in a small area of a device and can verify whether a suspicious point is, in fact, a defect.

Yet another alternative exists for locating power plane shorts. Once all other alternatives are exhausted, if the location of the short remains unknown, a sufficiently high current can be applied to blow the short. This high-current stress technique may sometimes be helpful. A category of shorts will still escape detection, however, using any or all of the conventional techniques discussed above. This category of shorts would include shorts which are large enough not to easily be blown by a current stress yet difficult to recognize visually. One possible example of a short in this category is an interlevel short which shorts two power planes vertically yet cannot be easily confirmed as a short visually with any certainty. To assure better yields and diagnostics, therefore, it would be desirable to provide an improved technique which can find this category of shorts.

Finally, a problem related to the task of locating power plane shorts exists: it is regularly necessary to determine whether or not a suspicious-looking defect is a short. The conventional techniques often cannot discern whether a particular defect shorts one layer of thin film to another. It would be desirable to verify whether these defect are in fact voltage plane shorts before attempting to repair them.

The deficiencies of the conventional techniques (e.g., IR imaging, magnetic imaging, pick-up coil imaging, current stress) used to locate power plane shorts show that a need still exists for an improved technique. That need is for a practical and convenient technique which can be used to detect, locate, and define inter-level shorts or otherwise difficult-to-recognize shorts. To meet that need and to overcome the shortcomings of the conventional techniques, a new apparatus and method to achieve these functions is provided.

An object of the present invention is to provide a practical and convenient technique for detecting, locating, and defining inter-level shorts or otherwise difficult-to-recognize shorts. A related object is to provide a practical and cost-effective apparatus and method to achieve these functions. Another object is to provide a convenient apparatus and method which integrate with existing quality control devices and processes.

SUMMARY OF THE INVENTION

To achieve these and other objects, and in view of its purposes, the present invention provides an apparatus for detecting, locating, or defining a short in a thin-film module. The apparatus includes a mechanical fixture supporting the module. A current source provides a current pulse to the module. Polarized light is directed onto the module, with an intermediate element disposed between the module and the source of the polarized light. A microscope is used to observe the module, facilitating identification of a short by the blinking of the polarized light intensity reflected from the photo-sensing element as the short expands and shrinks in response to the current pulse.

The intermediate element may be a stress birefringent coating (e.g., a polyimide insulating layer) disposed on the module and onto which the polarized light is directed. Alternatively, the intermediate element may be a magneto-optical Faraday rotator which responds to electromagnetic fields emanating from the short. The preferred rotator is a composite consisting of an iron garnet film which may be doped with at least bismuth to enhance the Faraday rotation, and which is grown epitaxially on a transparent nonmagnetic substrate and has a thin aluminum layer deposited on the iron garnet film surface.

The corresponding method of the present invention for detecting, locating, or defining a short in a thin-film module includes the following steps. First, a low frequency current is pulsed through the module. Polarized light from a light source is directed onto the module either through the above-mentioned stress birefringent coating disposed on the module or by utilizing a magneto-optical Faraday rotator disposed between the light source and the module. The module is observed. Finally, a short in the module is identified by the blinking of the polarized light intensity as the short expands and shrinks in response to, or produces Faraday photomagnetic-optic contrast synchronized to, the current pulse.

In one particular application of the method of the present invention, used to locate a voltage plane short in a thin-film module, the method is combined with conventional techniques. Initially, a conventional pick-up coil is provided and used to magnetically define the general location of the short. A conventional current stress apparatus is used to attempt to blow the short. Then, and if necessary, the steps of the method of the present invention are applied.

Finally, the method of the present invention can be applied as part of a method to destructively diagnose and locate a power plane short where the short is inside a ceramic chip module (or printed circuit board) and not on either the top or bottom of the module but rather is inside the module. The specific steps of the method in such an application include: (a) breaking the module into pieces; (b) locating the piece of the module with the power plane short; (c) pulsing a low frequency current through the piece of the module with the power plane short; (d) directing a polarized light from a light source onto the piece of the module with the power plane short through a magneto-optical Faraday rotator disposed between the light source and the module piece; (e) observing the module piece; (f) attempting to identify a short in the module piece by the blinking of the polarized light as the short expands and shrinks in response to the current pulse; (g) terminating the method if the short has been identified; (h) removing the magneto-optical Faraday rotator if the short has not yet been identified; (I) polishing the module piece; (j) checking the module piece to assure that a short has not been destroyed by the step (I) of polishing; and (k) repeating steps (c) through (j) until the short is either identified or destroyed.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
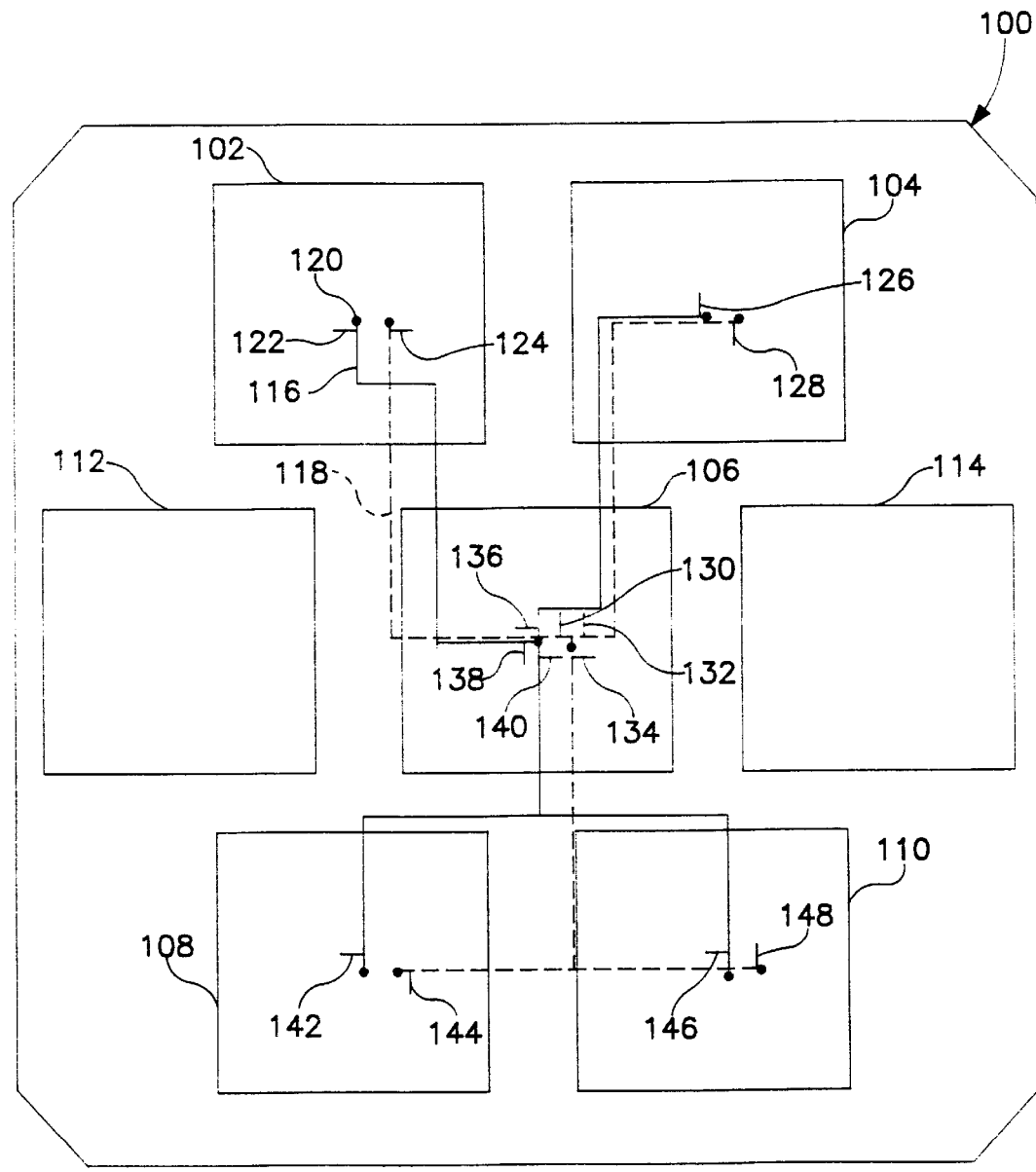
FIG. 1 is a plan view of a typical MCM.
Figure 2A:
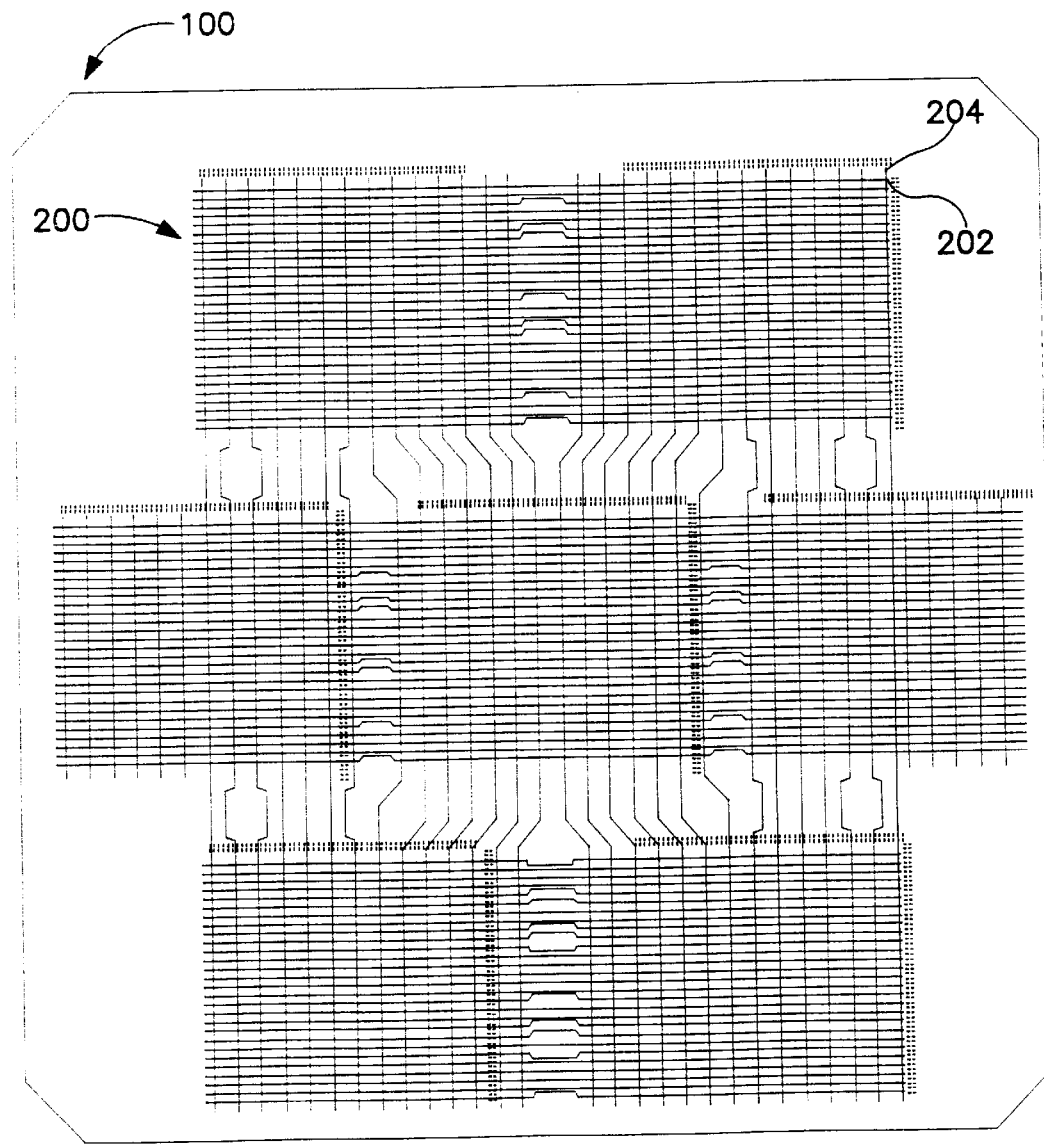
FIG. 2A is a plan view of a typical TSM repair net for the MCM of FIG. 1.
Figure 2B:
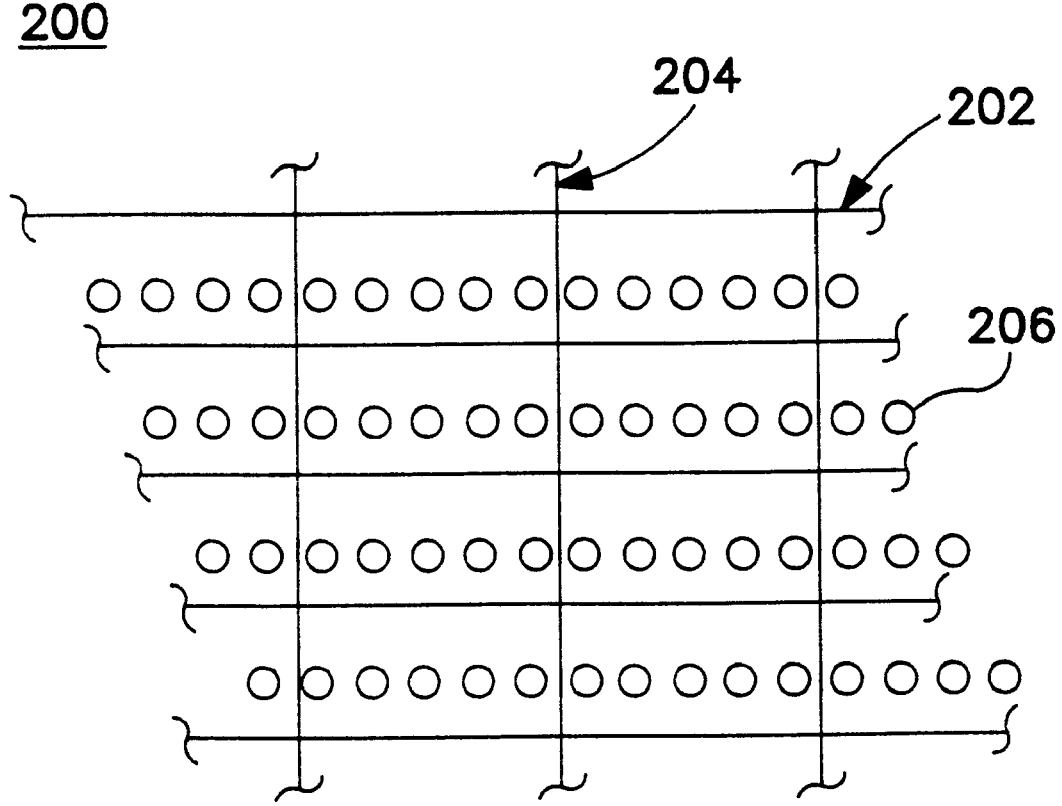
FIG. 2B is a detailed view of a portion of the repair net of FIG. 2A.
Figure 2C:
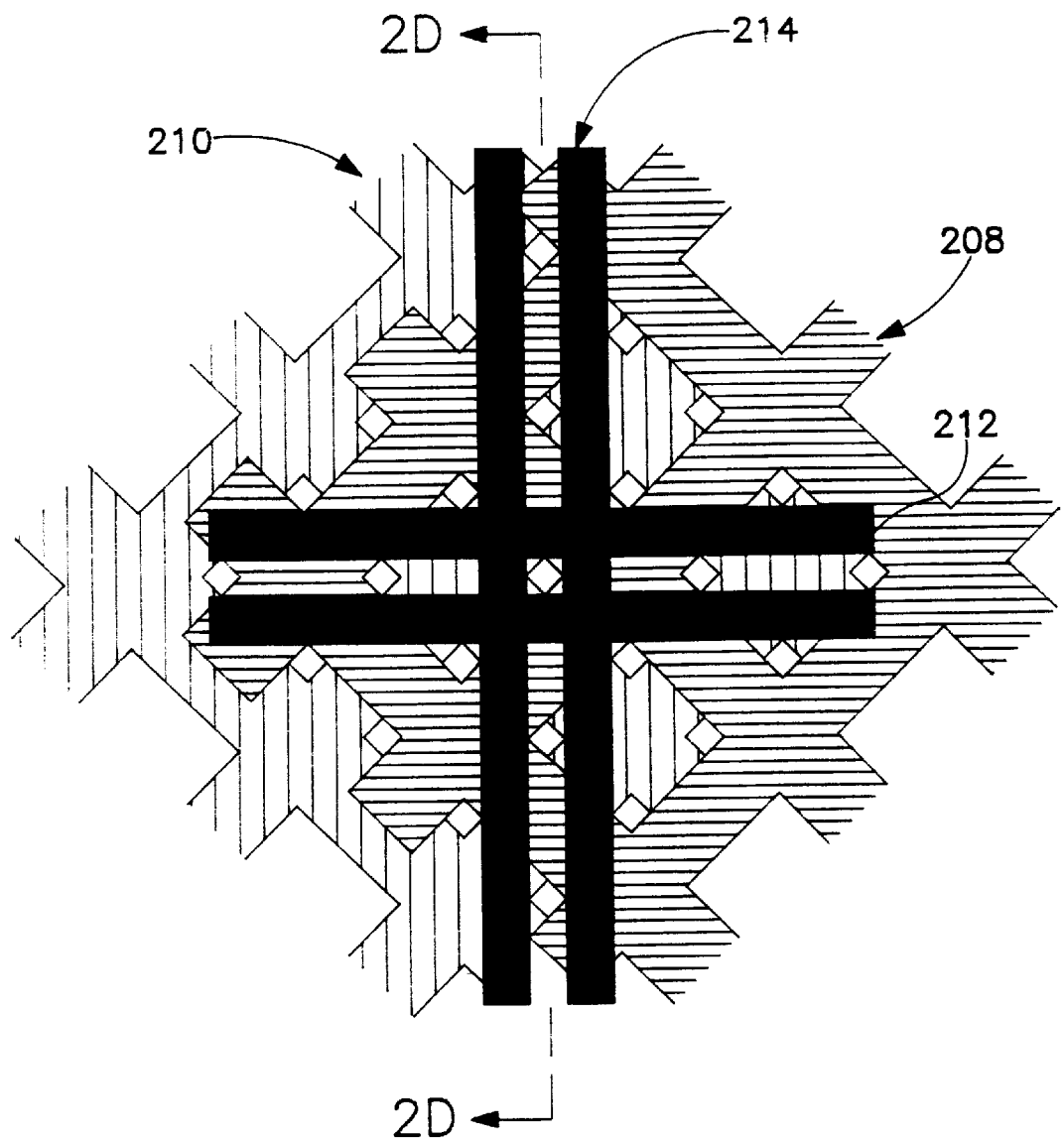
FIG. 2C is an x-ray view of a portion of the MCM of FIG. 2A.
Figure 2D:
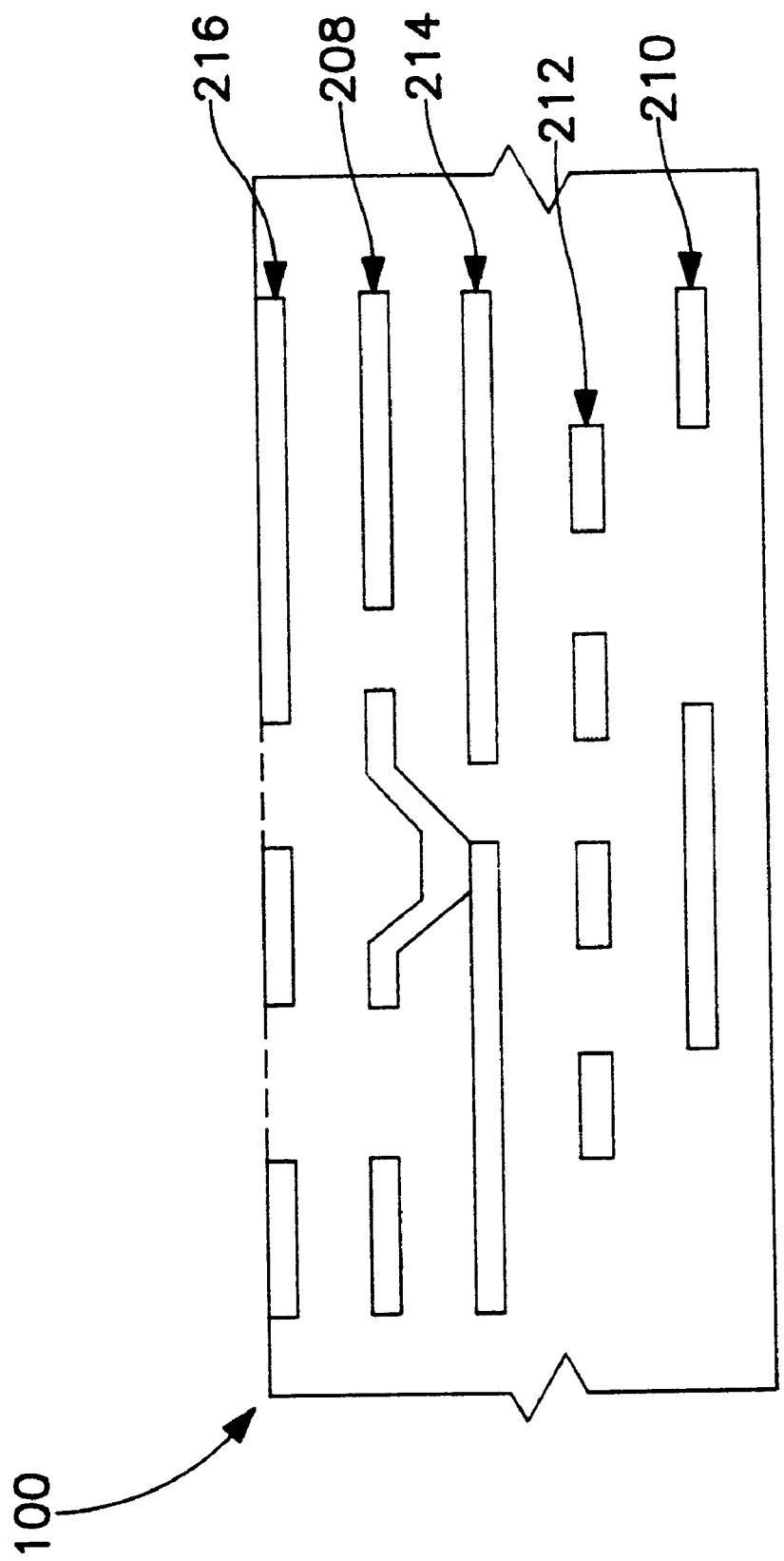
FIG. 2D is a cross-sectional view of FIG. 2C taken along the line 2D—2D.

The present invention uses polarized light optical microscopy and micro-ellipsometry to pinpoint thin-film power plane shorts on thin-film MCM substrates. The device is pulsed with a low frequency current source and examined under nearly cross-polarized light microscopy. The natural birefringence of the material of the device may be sufficient to pinpoint the short because the light will blink as the short slightly grows and shrinks. For some MCM substrates, the geometrical dimensions of the short are insufficient to simply apply polarized light microscopy successfully using the stress birefringence of the insulator. We may rotate the part under inspection 0 to 45 degrees to maximize the stress birefringence effect, which will be least in the direction of the stress and perpendicular to that direction but maximized at 45 degrees. Nevertheless, there will be some shorts by their nature where the geometrical dimensions of the short remain insufficient to simply apply polarized light microscopy successfully using the stress birefringence of the insulator.

An alternative way to use polarized microscopy to find these power to power shorts by visualizing the current flow is to use a magneto-optical Faraday rotator device, such as a mirrored iron garnet wafer, which can be inserted between the device and the microscope. The magnetic field produced by the pulsed current will provide a blinking effect which can be observed to precisely locate the short. The pulsing magnetic field around the current flow will cause the polarized light to twist up to 6 degrees in the iron garnet magneto-optical device and be visible using polarized microscopy. Once the short is precisely located, the iron garnet substrate may be removed and the same microscope can examine the defect in whatever conventional microscope lighting that may be desired.

A. Thermal-Mechanical Imaging of Thin-Film MCM Shorts Using Stress Birefringence with Polarized Microscopy Thermal-mechanical imaging using stress birefringence can be applied to locate a short in a thin-film MCM. Generally, birefringence is the property by which light propagates through a medium with different velocities for different states of light polarization. Polarized light is a light wave which has an electric vector, E (as opposed to its magnetic vector, H) polarized in a predictable fashion with respect to its plane of propagation. Unpolarized light has its E-vector oriented in a random or unpredictable fashion.

A medium through which light propagates may or may not alter the state of the polarization by itself. The medium may have a naturally active effect on the light and may by itself cause the polarization to change. Another type of medium, which by itself does not change the polarization state, may be induced to alter the polarization. Inducement in this method of MCM fault detection occurs due to the presence of a field or a mechanical stress. The method uses inducement from either or both electromagnetic fields and thermally induced strain generated by the current-conducting fault. The preferred embodiment for thermal mechanical imaging to locate a fault is to use a sensing medium which is optically isotropic, meaning that it does not by itself produce a change in the state of light polarization.

Strain birefringence is the effect in which stress acting on the medium locally changes the medium from an optically isotropic to an anisotropic medium. Thermal stress birefringence occurs when a heat distribution applied to the medium causes a strain birefringence, making the medium become anisotropic within the local region of temperature rise. In this region, light beams polarized parallel or perpendicular to the local strain axis propagate with different velocities. Strictly speaking, these are the two eigenmodes for propagation in a coating or film medium having plane parallel surfaces when the angle of illumination incidence is perpendicular to these surfaces. The two polarization components emerge from the film in the strained region having different phases due to this thermally induced anisotropic velocity of propagation.

In the preferred embodiment, the polarization of a single beam is aligned with its axis oblique to the strain axis, preferably at 45 degrees with respect to the strain axis. The beam thereby contains E-vector components both perpendicular and parallel to the strain axis, causing the beam emerging from the far side of the strained region to propagate having the two components out of phase. If the phase difference is 90 degrees, the light is circularly polarized. In general, the net summation of these two components in the outgoing beam produces elliptically polarized light. When passed through a polarizing element called the analyzer, an intensity contrast occurs between the localized region of elliptically polarized light due to strain and the background region of unaltered linear polarization which the crossed analyzer extinguishes (ideally) or at least suppresses. Elliptically polarized light caused by the thermal strain cannot be extinguished by the analyzer because the elliptically rotating E-vector contains components which on a time-average basis over a cycle time of oscillation lie parallel to the analyzer axis.

The intensity signal is best described as the contrast ratio of light intensity difference from the locally strained region compared with the general background region where no strain occurs, and divided by the background intensity. This ratio is strongest when the analyzer is set at or near to a right angle (crossed) alignment with respect to the polarizer. Thus, a microscopic view between crossed (or nearly crossed) polarizers produces an intensity variation revealing the location and nature of the local strain induced by heat from the current-conducting ground fault (the power plane short).

The growth and shrinking of the metal in a shorted net under pulsed current can often be seen under high-quality, crossed polarized microscopy. Many thin-film MCM devices use organic polyimide materials as the insulating layers. Organic polyimide materials tend to exhibit high amounts of stress birefringence. When a thin-film MCM device with an insulating layer of organic polyimide is examined under cross-polarized light, patterns of light are seen twisting almost everywhere, particularly around small structural edges;

Deposited film structures typically produce stress next to film edges. This stress produces a time invariant strain. Its background intensity in cross-polarized microscopy is a DC level of such background intensity against which the pulsating thermal strain is more difficult to detect. The strong steady background effect at the edge diminishes the contrast ratio for the pulsating thermal strain birefringence contrast. This diminished contrast ratio is possible to overcome by inserting an adjustable optical compensator into the microscope. This device introduces an adjustable amount of linear birefringence into either the illuminating or the observing optical beam path. An improved contrast ratio will result, therefore, when the compensator is inserted and adjusted for minimum intensity at these edges. Thereupon, pulsing the current in the fault will better detect the location of any fault which happens to lie next to such an edge.

Figure 3A:
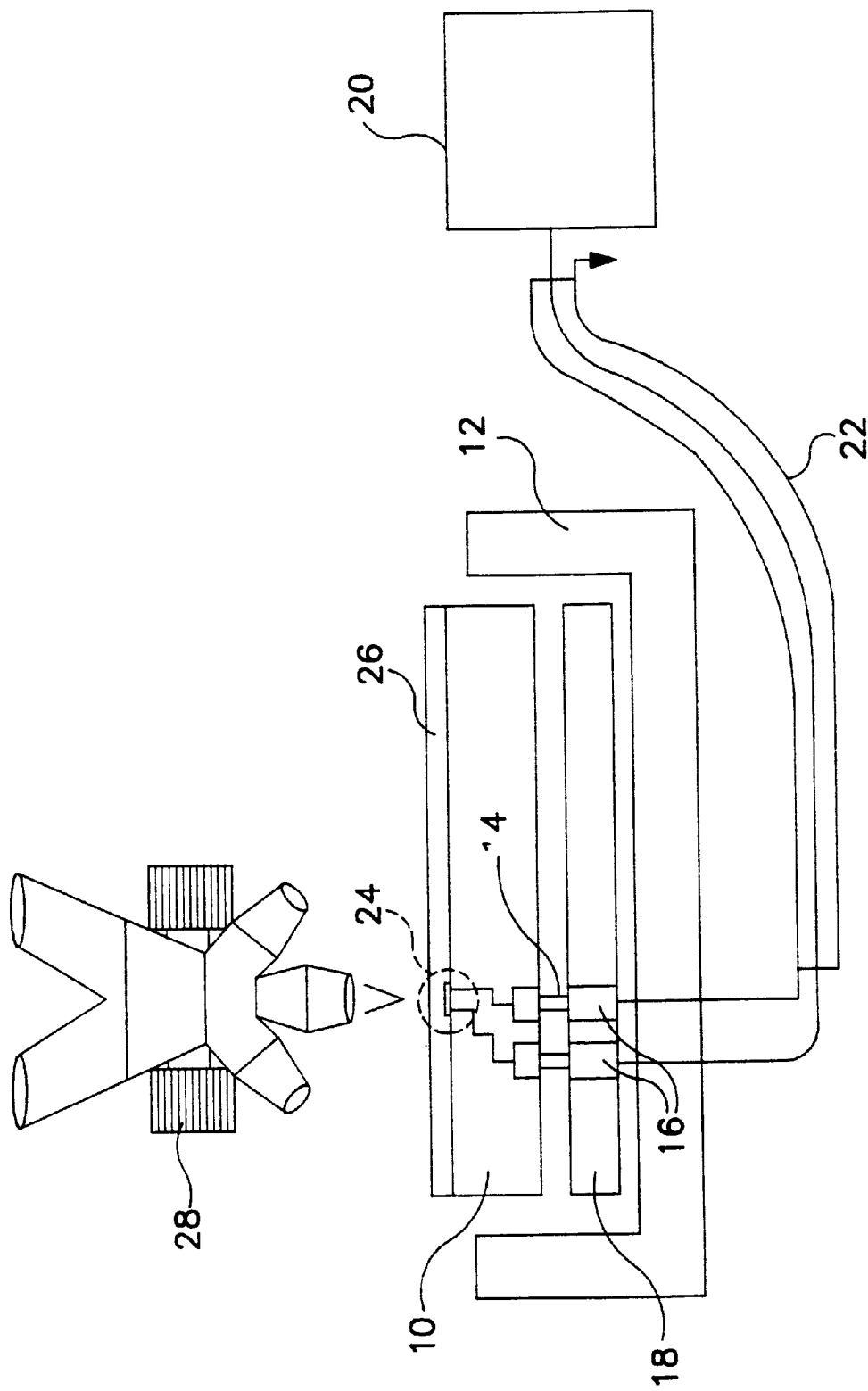
FIG. 3A illustrates an apparatus for imaging a short using stress birefringence according to a first embodiment of the present invention.

The apparatus and method according to a first embodiment of the present invention are illustrated in FIG. 3A. The apparatus and method are used to detect inter-level shorts in a thin-film MCM substrate 10. Thin-film MCM substrate 10 is placed in a mechanical fixture 12 which contacts the voltage plane pogo pins 14 of thin-film MCM substrate 10 with pogo connector pins 16. Pogo connector pins 16 are surrounded by insulation 18. A uni-polar current source 20 provides a current pulse to pogo connector pins 16, through coaxial cable 22, as current source 20 turns on and off at 5 pps.

As the current pulse travels through the short, the thin-film area 24 around and including the defect in thin-film MCM substrate 10 will heat and cool at 5 Hz. The cyclic heating and cooling of the defect causes it to expand and shrink slightly, in turn, causing an oscillating local stress in the polyimide insulating layer 26 of thin-film MCM substrate 10. The pulsating stress in the polyimide insulating layer 26 produces a pulsating visual intensity because of the pulsating elliptically polarized light caused by the induced strain. The light pulsations can be viewed by eye using cross-polarized microscopy. The twisted light can be viewed manually with a cross-polarizing microscope 28. A high-quality microscope such as a Zeiss Axiotron is suitable.

The method of the present invention offers a practical and convenient technique for detecting, locating, and defining inter-level shorts. The operator simply observes the pattern directly under cross-polarized light, looking at low power for a blinking effect. The human eye is very sensitive to blinking and the operator can see defect area 24 directly. The method of the present invention also integrates with existing quality control processes. For example, once the defect is found, the operator can switch microscope 28 to whatever other lighting may be appropriate to further study the defect.

Five hertz is a convenient frequency for the human eye to detect blinking. Defect area 24 will blink under a high-quality, cross-polarized microscope 28, particularly at low total magnifications such as 25× to 50×. Once the approximate defect area 24 is located, the operator can zoom to a higher magnification to view the defect and to diagnose the defect further. Thus, the apparatus and method of the present invention provide a practical way to find many voltage-to-voltage plane or IO-to-voltage plane shorts, particularly if the shorts are covered by polyimide layer 26.

In addition, even if polyimide is not part of the manufacturing process, one could coat a scrapped part having a short located at the surface of the part with a polyimide. The coated part would then be inspected according to the method of, and using the apparatus of, the present invention. In this case, the method and apparatus of the present invention would be used as a diagnostic.

Figure 3B:
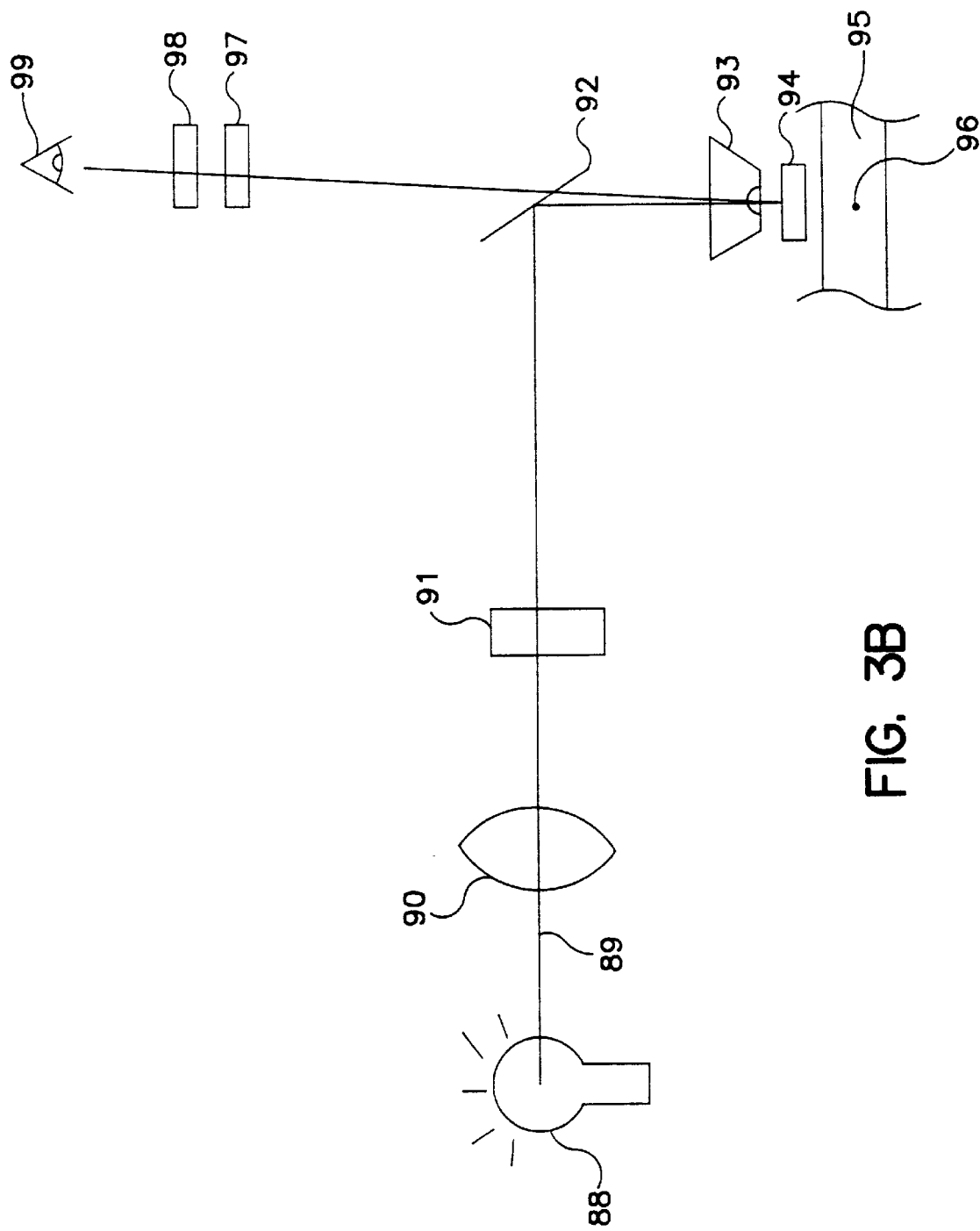
FIG. 3B illustrates an alternative apparatus for imaging a short using stress birefringence according to the first embodiment of the present invention.

FIG. 3B illustrates an alternative apparatus for imaging a short using stress birefringence according to the first embodiment of the present invention. A light source 88 provides a light ray 89, which passes through a Koehler Optics collimator 90 and an optical polarizer 91, before engaging a beam splitter 92. Light ray 89 is directed by beam splitter 92 toward an objective lens 93 and, in turn, onto a magneto-optic sensor film 94. Magneto-optic sensor film 94 is disposed over the multi-layer circuit 95 under inspection. A ground fault 96 is shown to exist inside multi-layer circuit 95. Light ray 89 returns from magneto-optic sensor film 94, passing through an optical compensator 97 and an optical analyzer 98, to a human eye or camera 99 for visual detection.

B. Incorporation Of An Iron Garnet Mirror

Not all geometric designs and materials exhibit sufficient stress birefringence to allow direct viewing of the current heating in shorted device area 24. This problem can be overcome by incorporating a magnetic mirror comprised of iron (Fe) garnet in the apparatus of the present invention. When iron garnet is grown on a garnet substrate, the iron garnet acts as a Faraday rotator and twists polarized light in the presence of a magnetic field. The Faraday effect is the rotation of the plane of polarization of a beam of linearly polarized light when the light passes through matter in the direction of the lines of force of an applied magnetic field. Rotation of the plane of polarization occurs when there is a difference between the indices of refraction $n^+$ for right-handed polarized light and $n^-$ for left-handed polarized light. Discovered by Michael Faraday in 1846, the effect is often called magneto-optic rotation.

Figure 4:
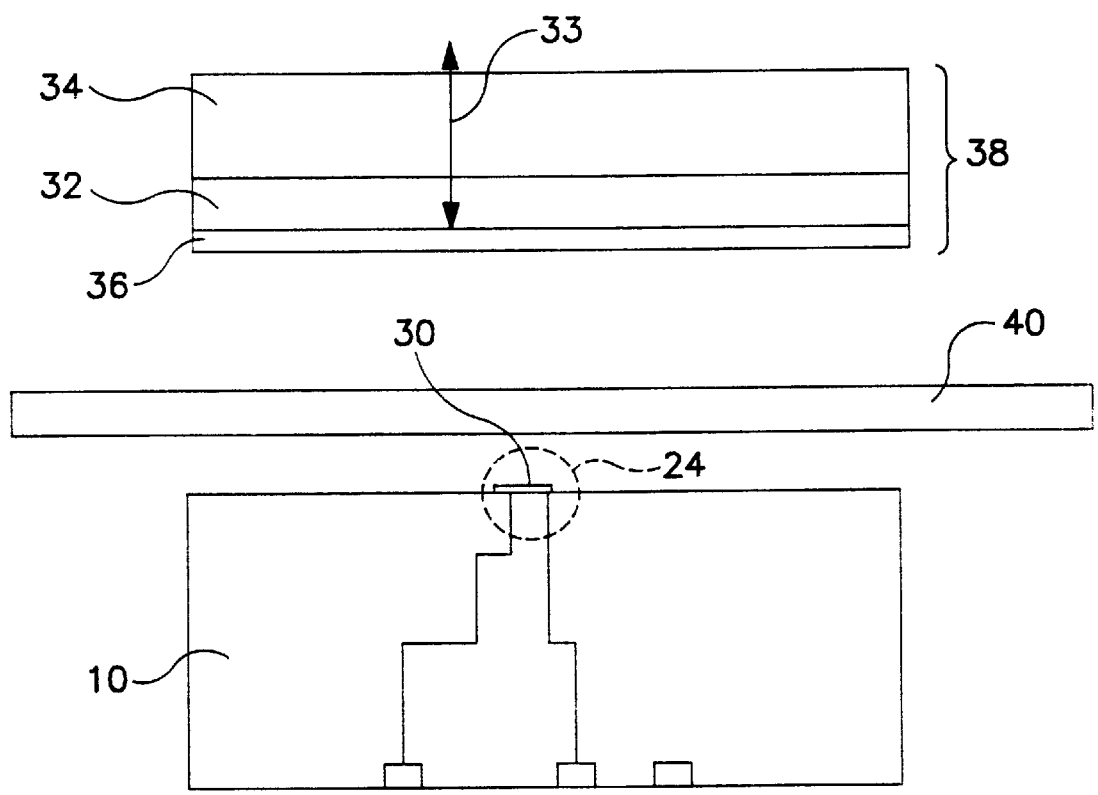
FIG. 4 shows an iron garnet composite which is used, according to a second embodiment of the present invention for imaging a short using stress birefringence.

According to the present invention and as illustrated in FIG. 4, iron garnet 32 is grown on garnet 34 and the iron garnet 32 is mirrored with about 1,000 Angstroms of aluminum 36 to form a composite 38. Next, the mirrored side of composite 38 is placed on top of a 25 to 50 micron (1–2 mil) thick polyester sheet 40 which, in turn, is placed on top of thin-film MCM substrate 10. Sheet 40 may be made of Mylar® material having great tensile strength. A sample light path through composite 38 is illustrated at 33.

Figure 5:
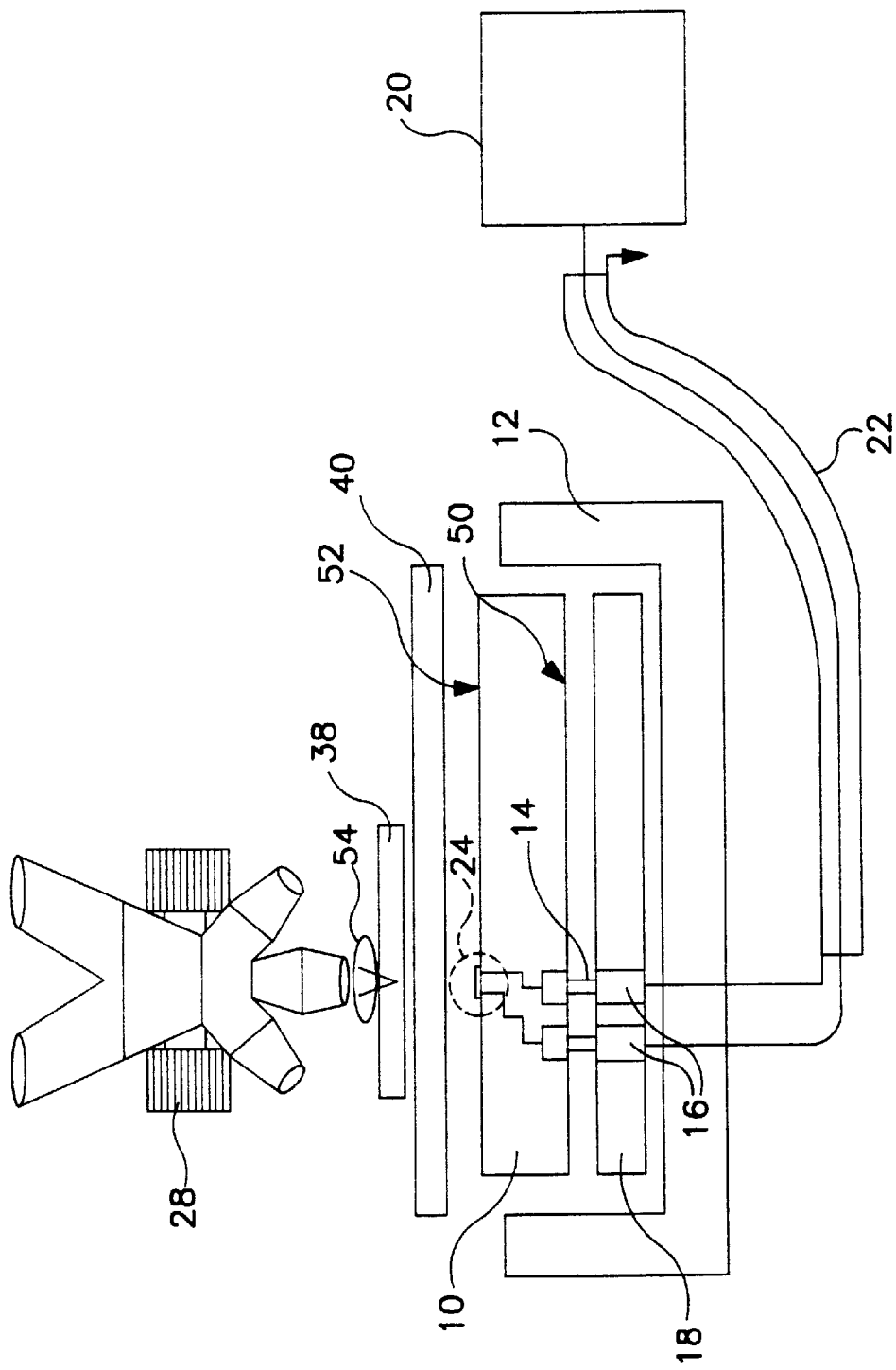
FIG. 5 illustrates an apparatus for imaging a short using stress birefringence according to the second embodiment of the present invention, incorporating the iron garnet composite shown in FIG. 4.

The apparatus and method according to the second embodiment of the present invention are illustrated in FIG. 5. The apparatus and method are used to detect inter-level shorts in a thin-film MCM substrate 10. Thin-film MCM substrate 10 is placed in a non-destructive, mechanical fixture 12 which contacts the voltage plane pins 14 of thin-film MCM substrate 10 with pogo connector pins 16. Pogo connector pins 16 are surrounded by insulation 18. Thinfilm MCM substrate 10 has BSM (bottom side metallurgy) pads 50 and TSM (top side metallurgy) pads 52. Current source 20 provides a current, between 0.2 to 2A pulsed on and off in a square wave fashion at 5 Hz, through cable 22 and pogo connector pins 16 to short 30 in defect area 24.

Sheet 40 is placed over TSM pads 52 of thin-film MCM substrate 10 in defect area 24 where thin-film short 30 is located. Mirrored iron garnet film composite 38 is placed, with the mirrored side down, on sheet 40 just above thin-film MCM substrate 10. Using a 2.5× or 5×, low-power, is Neoflor®, strain-free objective lens or some other objective lens suitable for high-quality polarized microscopy, defect area 24 of thin-film MCM substrate 10 is observed under cross polarized or elliptically polarized light. If short 30 is highly localized, a blinking effect in the vicinity of short 30 will be easily seen at low power due to the ability of the iron garnet to act as a Faraday rotator. Once short 30 is located by its characteristic blinking, the operator may remove mirrored iron garnet composite 38 and observe defect 30 (see FIG. 4) directly for diagnostic or repair purposes. Alternatively, sheet 40 may be removed or one could inspect through it.

As an example for use in the apparatus and method of the present invention, three types of composite 38 are recommended. Each type of composite 38 has an iron garnet film grown on a garnet substrate. Aluminum is cold sputtered over the iron garnet to mirror the surface. The aluminum is deposited at a thickness of about 100 nm and then covered with a protective layer of about 1,000 Angstroms of silicon dioxide ($SiO_2$). Each of the three recommended types of composite 38 is described below.

The first type of composite 38 has an iron garnet film having in-plane anisotropy and is doped with at least bismuth. The first composite 38 can be magnetically saturated with a 10–20 Oersted, in-plane field, and has a coercivity (Hc) on the order of 0.1 Oersted. The first composite 38 can detect, by magneto-optic imaging using a polarizing microscope, the location of a current conductor carrying at least 20 mA but less than 100 mA when the conductor line is located no less than 25 microns away from the first composite 38 and is parallel to the first composite 38. The magneto-optic image will detect the location of the conductor line within a range of about 200 microns but preferably within 100 microns.

The first composite 38 is deposited on a non-magnetic substrate (or wafer), and preferably would contain few, if any, defects. The first composite 38 is deposited as a film on a 76 mm (3 inch) diameter substrate (or wafer) and should contain less than five defects per square inch. The substrate should be largely transparent in the visible wavelength region. Because the first composite 38 contains iron ions, only partial transparency in the visible region is expected. The thickness of the first composite 38 is between 3 to 5 microns, to enable imaging with intense visible light from a 100 Watt mercury arc, and nearly cross polarized in a high-quality microscope. Less intense (and generally safer), conventional microscope halogen bulbs may be used in a very high quality polarized microscope but the effect will be weaker. Throughout this specification, by iron-garnet, FeGarnet or YIG it is meant Bi:YIG which is yttrium iron garnet substituted with at least bismuth. In general, other non-magnetic atoms such as gallium and aluminum are understood to be available as substitutents to control the intrinsic magnetic saturation induction and the magnetic anisotropy, where preferable. Atomic substituents in a non-magnetic substrate such as gadolinium gallium or gadolinium aluminum garnet may also be used to reduce the lattice mismatch and strain when a magnetic garnet film is being deposited.

The second type of composite 38 incorporates one or two, tilted, uniaxial films. One film has its uniaxis tilted 15 degrees from the perpendicular to the substrate; the other film has a 30-degree tilt. The domain patterns in one or both of these two films should exhibit straight parallel domains which respond to uniform applied fields as follows: an in-plane DC field coupling to the in-plane component of tilted magnetization causes the stripe pattern to be oriented parallel to the field, while an out-of-plane DC field couples to the perpendicular component of magnetization causing the stripe pattern to increase its spatial repeat distance (pattern period). This type of tilted uniaxis film has been reported by T. Johansen, D. Norman & E. Turok, Variation of Stripe-Domain Spacing in a Faraday Effect Light Deflector, 42 J. Applied Physics, No. 4, at 1715–16 (Mar. 15, 1971), for the application of magnetically controllable laser beam deflection.

The thickness and domain widths for the second composite 38 should be a few microns (approximately 3–5 microns). The remainder of the properties for the second composite 38 should be the same or similar to those described above for the first composite 38. Specifically, the second composite 38 should have low coercivity and should be doped with at least bismuth to provide high Faraday rotation.

The third type of composite 38 is a bi-layer film. One layer is an in-plane, anisotropic iron garnet film. The other layer is a perpendicular, anisotropic, uniaxial, at least bismuth-doped, iron garnet film. The two layers are grown epitaxially, one after the other, without any other layer between them. The perpendicular uniaxial film layer exhibits magnetic bubble or cylinder domains when a bias field is applied perpendicular to the film plane. The application of an in-plane field causes translation of the domain walls separating large domains in the in-plane anisotropic film.

The coercivity of the in-plane anisotropic film should be less than 0.1 Oersted; in the perpendicular uniaxis film, the coercivity should be less than 1.0 Oersted. The magnetic bubbles should have a diameter of between 4 and 7 microns. There should be exchange and magneto-static coupling between the two films such that, when in-plane domain walls are moved by application of an in-plane field, the in-plane domain walls can capture and hold on to the bubble domains which they intersect in the adjacent uniaxial film. The third composite 38 is the most sensitive of the three types to a shorted conductor inducing field component parallel to the film plane. The widely separated domain walls of the in-plane anisotropic sublayer in this composite are easily moved large distance by small changes of in-plane fields. The attached bubbles having magnetization components perpendicular to the film and parallel to the light propagation direction, produce the full maximum in Faraday contrast. The attendant motions of the bubble domains attached to the moving walls of the in-plane domains are readily discernible in a polarizing microscope. The Faraday contrast from the domains in the in-plane anisotropy layer is essentially absent unless the microscope is set up for oblique illumination, in place of perpendicular illumination. However, this composite requires the use of a bias magnetic field, typically 25–150 Oe, applied perpendicularly to the composite to stabilize bubbles. The bubbles should be mobile cylinder rather than stripes or dog bones whose motions are primarily controlled by interaction with each other. It is less desirable when the interactions with each other (other bubbles) are much stronger than the interactions with the in-plane domains. This bubble-to-bubble interaction is reduced by simply making the bubble-to-bubble spacing larger. Spacing is increased by reducing the bubble density. This occurs when the bias field is increased until some of the bubbles disappear by collapsing. The bubble domains remaining are yet stable in the presence of a bias field. An air core coil and current supply are used to provide the necessary DC bias field for this third composite.

Microscope 28 may be used in the apparatus of the present invention with an arc lamp for research, development, or controlled manufacturing applications. A tungsten-halogen white light source is recommended, however, for typical manufacturing use. The tungsten-halogen white light source has some advantages, avoiding safety risks to manufacturing operators, although it makes the method slightly less sensitive to magnetic fields than the arc lamp. In addition, current source 20 may provide a bipolar current pulse rather than a unipolar current pulse. When used with a white light illumination, a bipolar current pulse will provide a color variation in addition to an intensity blink.

The effect is attributed to the wavelength dependence of the Faraday rotation which is particularly strong in at least bismuth doped iron garnet materials. This Faraday dispersion in combination with observations using nearly but not completely crossed polarizers produce a color shading for oppositely oriented perpendicular magnetic components. Opposing currents during a bipolar pulse produce opposing perpendicular fields causing opposite perpendicular magnetization components.

An additional, structural variation is envisioned for the apparatus of the present invention. Electrical windings such as in a 4-pole electric motor 54 may be provided. The windings produce magnetic fields which, when powered with AC current at the proper phase, produces a rotating magnetic field. As illustrated in FIG. 5, motor winding 54 adds a rotating field at 60 Hz (such as would make a compass spin if placed above the stage of microscope 28) with an additional biasing magnet if desired. The degree to which the windings of motor 54 enhance the apparatus of the present invention will depend on the geometry of the components of the apparatus, the application process, and the quality of the iron garnet. The superposition of a rotating field may increase the sensitivity of the iron garnet device and enhance its ability to visualize weak magnetic fields, thus allowing operation at lower currents. A composite 38 of the first or third type, as described above, is suitable for use in conjunction with motor winding 54.

Figure 6:
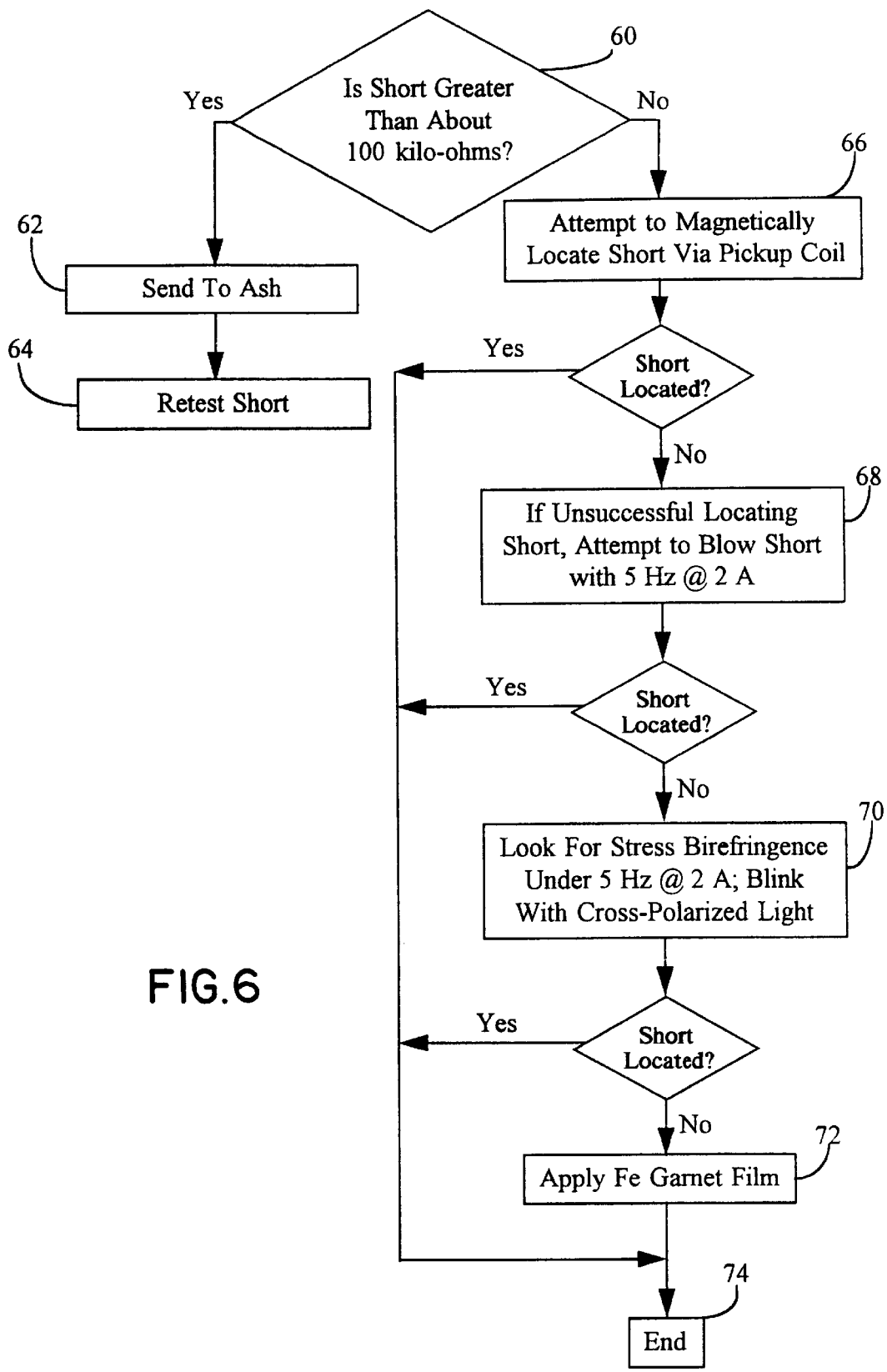
FIG. 6 is a flow diagram outlining a general method, incorporating the steps of the method of the present invention, that can be used to find voltage plane shorts.

FIG. 6 is a flow diagram outlining a general method that can be used to find voltage plane shorts. The method sequentially applies conventional techniques (e.g., the magnetic pick-up coil and current stress approaches) then the cross-polarization techniques of the present invention. At Step 60, the short is analyzed to determine whether the short is more than about 100 kΩ. If so, then thin-film MCM substrate 10 is subjected to an ashing process (Step 62). During the ashing process, thin-film MCM substrate 10 is exposed to a plasma (typically the plasma is a mixture of nitrogen and oxygen) which removes a thin haze or film from thin-film MCM substrate 10 to clean it. The short is retested at Step 64.

If the short is not more than about 100 kΩ, a magnetic pick-up coil technique is applied, at Step 66, to attempt to locate the short. A current stress technique is applied, at Step 68, if the magnetic technique is unsuccessful. The two embodiments of the cross-polarization method of the present invention are applied if the current stress technique also proves unsuccessful. At Step 70, the first embodiment (without iron garnet mirror composite 38) is applied. If necessary, at Step 72, the second embodiment (with iron garnet mirror composite 38) is applied to locate the short.

One application of the apparatus and method of the present invention involves locating brick shorts for diagnostic reasons. A brick is defined as a ceramic MCM package and may have a short inside it. A short located inside a ceramic brick or some other type of electronics package, which is not on the surface of the brick or package, is especially difficult to find. Using conventional processes to locate the short, a diagnostic person may spend a full day to precisely locate the short by breaking the brick, polishing it, and applying inspection techniques. Moreover, if the diagnostic person is not careful, the short can be polished through and diagnosis may be impossible.

Accordingly, a method which would allow the diagnostic person to see a short 1–2 mils below the surface being polished and to approximately locate the short would be desirable. Such a method is outlined, in the form of a flow diagram, in FIG. 7. The method incorporates iron garnet mirror composite 38 after each stage of polishing and allows the diagnostic person to see whether polishing has reached the vicinity of the short. Composite 38 works best with inspection relatively near (50–100 microns) the short; this requirement helps the diagnostic person to avoid over polishing through the short. A composite 38 of the first or third type, as described above, is suitable for use in conjunction with this method.

Figure 7:
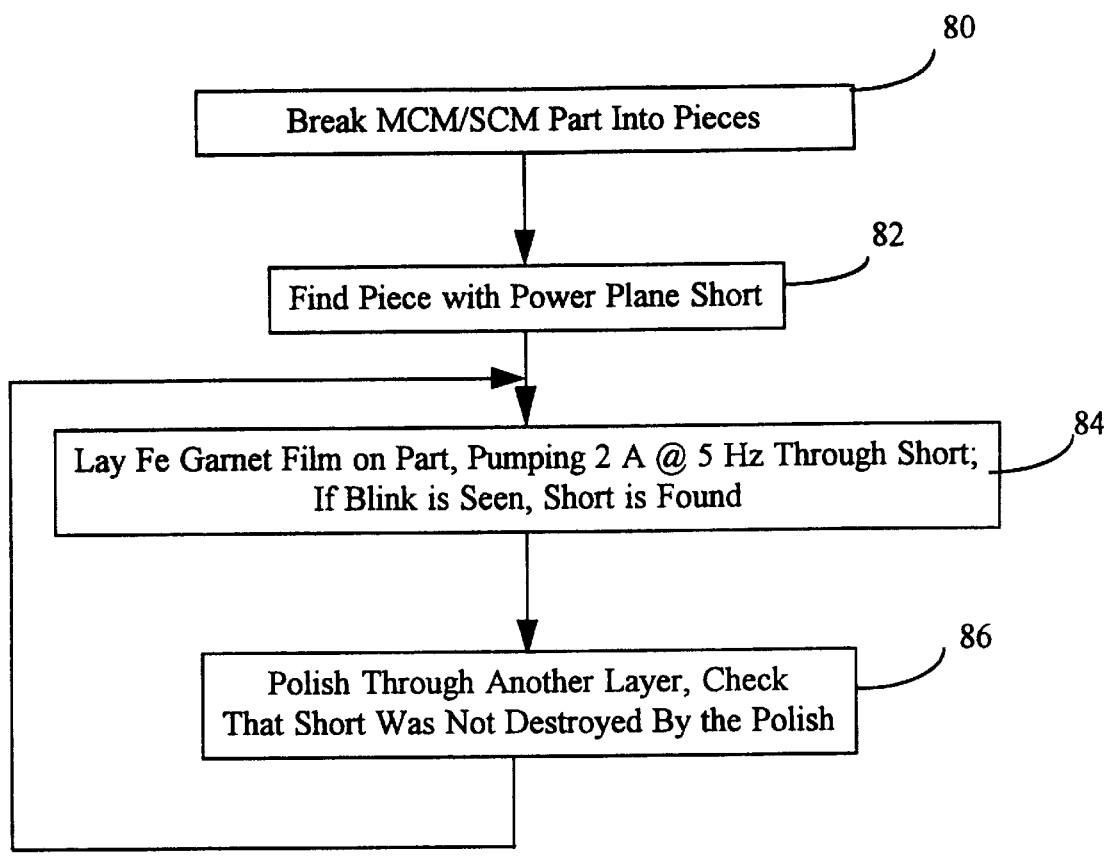
FIG. 7 is a flow diagram illustrating one application of the apparatus and method of the present invention in which brick shorts are located for diagnostic reasons.

Specifically, as illustrated in FIG. 7, a ceramic single chip module (SCM) or MCM package having a short is broken into pieces in Step 80. The piece with the power plane short is located in Step 82. The second embodiment of the method of the present invention described above (in which iron garnet mirror composite 38 is provided on the piece to be inspected) is applied to locate the short in Step 84. If blinking is observed, the short is found. On the other hand, if the short is not discovered in Step 84, iron garnet mirror composite 38 is removed and the piece is polished through another layer in Step 86. Also as part of Step 86, the piece is checked to assure that the short was not destroyed by the last polish. The method returns to repeat Steps 84 and 86 until the short is either found or destroyed.

Additionally, we can also envision using a liquid colloidal preparation whereby a YIG based paint could be applied directly to the surface of the electronic module under inspection rather than using a garnet substrate. This may be useful for diagnostic purposes.

There are other magneto-optic effects which can in principle be used to detect power plane shorts. One is the magnetic circular dichroism effect (MCD) This is due to the difference between a material's optical absorption coefficient (rather than index of refraction as in the Faraday effect) for right and left circularly polarized light. Like the Faraday effect, MCD also varies linearly with the magnetization component along the light propagation direction. Some materials, such as EuSe at cryogenic temperatures, have a very large MCD at visible wavelengths. If a material becomes available with a large MCD at room temperature, films made of this material could also be used for this application and detect power plane shorts.

A second magneto-optical effect which could be useful, is the Cotton-Mouton effect, or magnetic linear birefringence. It is described as a difference in index of refraction for light polarized parallelly and perpendicularly to the magnetization when the magnetization lies in the plane perpendicular to the light propagation. Maximum sensitivity to a magnetic reorientation occurs when the plane of light polarization is oriented 45 degrees from the natural orientation of the magnetization and this magnetization lies in the plane perpendicular to the axis of light propagation. This magnetic linear birefringence is proportional to the square of the magnetization and being a second order effect, is usually weaker than the Faraday effect. As in the case of thermal stress birefringence which is also due to a linear birefringence, contrast will be enhanced with the use of an adjustable optical compensator.

Other applications of the apparatus and method of the present invention abound. In some cases, a suspicious area is found, a bad laser repair is likely, or an inter-level short is suspected and it becomes necessary to confirm whether the area is indeed the short or not. Many times small laser mask defects may give rise to small ILS-type defects and it would be desirable to confirm whether one was indeed a short. The apparatus and method of the present invention may be applied to provide such confirmation.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. The apparatus and process of the present invention may be applied, for example, to locate shorts other than power plane shorts.

What is claimed:

1. An apparatus for detecting, locating, or defining a short in a thin-film module, the apparatus comprising:

a mechanical fixture supporting the module;

a current source providing a current pulse to the module;

means for directing a polarized light onto the module;

an intermediate element disposed between the module and the directing means, the intermediate element being a stress birefringent coating disposed on the module or a magneto-optical Faraday rotator; and means for observing the module, the observation means facilitating identification of a short by the blinking of the polarized light as the short expands and shrinks in response to the current pulse.

2. The apparatus of claim 1 wherein the module has voltage plane pins and the mechanical fixture has connector pins, surrounded by insulation, engaging the voltage plane pins.

3. The apparatus of claim 2 wherein the current source provides the current pulse to the connector pins of the mechanical fixture which, in turn, provide the current pulse to the voltage plane pins of the module.

4. The apparatus of claim 1 wherein the current source provides a current pulse of between about 0.2 and 2A at about 5 Hz.

5. The apparatus of claim 1 wherein the stress birefringent coating is a polyimide insulating layer.

6. The apparatus of claim 1 wherein the rotator is a composite having a garnet substrate, an iron garnet film disposed on the substrate, and a thin aluminum mirror layer disposed on the iron garnet film.

7. The apparatus of claim 6 wherein the composite rotator has a protective overcoat disposed over the thin aluminum mirror layer.

8. The apparatus of claim 1 further comprising a electric winding disposed between the directing means and the rotator.

9. The apparatus of claim 1 further comprising a thin polyester sheet disposed between the rotator and the module.

10. The apparatus of claim 1 wherein the observation means is a microscope having a low-power setting of less than about 50×.

11. An apparatus for detecting, locating, or defining a voltage plane short in a thin-film multi-chip module having voltage plane pins, the apparatus comprising:

a stress birefringent coating disposed on the module;

a mechanical fixture supporting the module and having connector pins, surrounded by insulation, which engage the voltage plane pins;

a current source providing a current pulse to the connector pins of the mechanical fixture which, in turn, provide the current pulse to the voltage plane pins of the module; and a microscope directing a polarized light onto the stress birefringent coating on the module and allowing observation of the module, the microscope facilitating identification of a short by the blinking of the polarized light in response to the current pulse.

12. An apparatus for detecting, locating, or defining a voltage plane short in a thin-film multi-chip module having voltage plane pins, the apparatus comprising:

a mechanical fixture supporting the module and having connector pins, surrounded by insulation, which engage the voltage plane pins;

a current source providing a current pulse to the connector pins of the mechanical fixture which, in turn, provide the current pulse to the voltage plane pins of the module;

a magneto-optical Faraday rotator;

a microscope directing a polarized light onto the magneto-optical Faraday rotator disposed between the microscope and the module, and allowing observation of the rotator, the microscope facilitating identification of a short by the blinking of the polarized light in response to the current pulse; and a magneto-optical Faraday rotator disposed between the microscope and the module.

13. A method for detecting, locating, or defining a short in a thin-film module, the method comprising:

pulsing a low frequency current through the module;

directing a polarized light from a light source onto the module through one of a stress birefringent coating disposed on the module and a magneto-optical Faraday rotator disposed between the light source and the module;

observing the module; and identifying a short in the module by the blinking of the polarized light as the short expands and shrinks in response to the current pulse.

14. The method of claim 13 wherein the polarized light is directed onto the module through a magneto-optical Faraday rotator and the method further comprises inserting a thin polyester sheet between the rotator and the module.

15. The method of claim 14 further comprising the step of inserting a electrical winding between the light source and the rotator.

16. The method of claim 13 wherein the step of observing the module is performed with a microscope and the method further comprises setting the microscope to a low-power setting of less than about 50×.

17. The method of claim 13 wherein the low frequency current is pulsed through the module between about 0.2 and 2A at about 5 Hz.

18. A method for locating a voltage plane short in a thin-film module, the method comprising:

providing a pick-up coil;

using the pick-up coil to magnetically define the general location of the short;

attempting to blow the short with a current stress apparatus;

pulsing a low frequency current through the module;

directing a polarized light from a light source onto the module through one of a stress birefringent coating disposed on the module and a magneto-optical Faraday rotator disposed between the light source and the module;

observing the module; and identifying the short in the module by the blinking of the polarized light in response to the current pulse.

19. A method for locating a voltage plane short in a thin-film module, the method comprising:

providing a pick-up coil; using the pick-up coil to magnetically define the general location of the short;

attempting to blow the short with a current stress apparatus;

pulsing a low frequency current through the module;

directing a polarized light from a light source onto the module through a stress birefringent coating disposed on the module;

observing the module;

attempting to identify the short in the module by the blinking of the polarized light in response to the current pulse;

terminating the method if the short has been identified;

pulsing a low frequency current through the module if the short has not yet been identified;

directing a polarized light from a light source onto the module through a magneto-optical Faraday rotator disposed between the light source and the module;

observing the module; and identifying the short in the module by the blinking of the polarized light as the short expands and shrinks in response to the current pulse.

20. A method of diagnosing a power plane short in a ceramic chip module, the method comprising:

(a) breaking the module into pieces;

(b) locating the piece of the module with the power plane short;

(c) pulsing a low frequency current through the piece of the module with the power plane short;

(d) directing a polarized light from a light source onto the piece of the module with the power plane short through a magneto-optical Faraday rotator disposed between the light source and the module piece;

(e) observing the module piece;

(f) attempting to identify a short in the module piece by the blinking of the polarized light as the short expands and shrinks in response to the current pulse;

(g) terminating the method if the short has been identified;

(h) removing the magneto-optical Faraday rotator if the short has not yet been identified;

(I) polishing the module piece;

(j) checking the module piece to assure that a short has not been destroyed by the step (I) of polishing; and (k) repeating steps (c) through (j) until the short is either identified or destroyed.

* * * * *